United States Patent
Lee et al.

(10) Patent No.: US 9,134,287 B2
(45) Date of Patent: Sep. 15, 2015

(54) SYSTEM FOR PROVIDING FOOD EXPIRATION DATE INFORMATION USING TTI AND METHOD FOR PROVIDING FOOD EXPIRATION DATE INFORMATION USING THE SAME

(75) Inventors: Seung Ju Lee, Seoul (KR); Kwang Won Hong, Seoul (KR); Jin Young Han, Seoul (KR); Seung Won Jung, Gyeonggi-do (KR)

(73) Assignee: Dongguk University Industry-Academic Cooperation Foundation, Seoul (KR)

(*) Notice: Subject to any disclaimer, the term of this patent is extended or adjusted under 35 U.S.C. 154(b) by 420 days.

(21) Appl. No.: 13/806,066

(22) PCT Filed: Apr. 27, 2011

(86) PCT No.: PCT/KR2011/003087
§ 371 (c)(1),
(2), (4) Date: Jan. 15, 2013

(87) PCT Pub. No.: WO2011/162477
PCT Pub. Date: Dec. 29, 2011

(65) Prior Publication Data
US 2013/0209615 A1  Aug. 15, 2013

(30) Foreign Application Priority Data
Jun. 23, 2010 (KR) .................. 10-2010-0059511

(51) Int. Cl.
*G01N 33/02* (2006.01)
*G06Q 10/08* (2012.01)

(52) U.S. Cl.
CPC .............. *G01N 33/02* (2013.01); *G06Q 10/087* (2013.01)

(58) Field of Classification Search
CPC ... G01N 33/02; G06Q 10/087; G06Q 10/083; G06Q 10/0832; G06Q 10/0838
USPC ........................................... 426/88; 374/102
See application file for complete search history.

(56) References Cited

U.S. PATENT DOCUMENTS 3,768,976 A * 10/1973 Hu et al. .................. 422/402
5,057,434 A * 10/1991 Prusik et al. ................. 436/2
(Continued)

FOREIGN PATENT DOCUMENTS

| JP | 2009048593 | 3/2009 |
| KR | 1020080110050 | 12/2008 |
| KR | 1020100064675 | 6/2010 |

OTHER PUBLICATIONS

Tsironi et al., "Application and Validation of the TTI Based Chill Chain Management System SMAS (Safety Monitoring and Assurance System) on Self Life Optimization of Vacuum Packed Chilled Tuna," International Journal of Food Microbiology, dated 2008, vol. 128, pp. 108-115 (8 pgs.).

(Continued)

*Primary Examiner* — Lisa Caputo
*Assistant Examiner* — Philip Cotey
(74) *Attorney, Agent, or Firm* — Timothy S. Westby; Porter Hedges LLP

(57) ABSTRACT

The present invention relates to a system for providing food expiration date information using a TTI (time temperature integrator) and a method for providing food expiration date information using the same. The system for providing the food expiration date information and the method for providing the food expiration date information using the same of the present invention includes: an input unit for receiving TTI information, food information, and distribution history information; a calculation unit for producing a TTI indication value corresponding to an expiration date of the food; and an output unit which determines and outputs a color corresponding to the expiration date of the food among stages of colors which can be expressed through the TTI according to time and temperature conditions using the TTI indication value. According to desired embodiments, the present invention enables a consumer to confirm correctly the expiration date of the corresponding food by providing the TTI indication value corresponding to the expiration date of the food.

15 Claims, 7 Drawing Sheets

(56) References Cited

U.S. PATENT DOCUMENTS

| | | | | |
|---|---|---|---|---|
| 7,612,325 | B1* | 11/2009 | Watkins et al. | 250/222.2 |
| 2002/0042734 | A1* | 4/2002 | Shikida et al. | 705/10 |
| 2002/0154574 | A1* | 10/2002 | Ector et al. | 368/89 |
| 2004/0100380 | A1* | 5/2004 | Lindsay et al. | 340/540 |
| 2005/0081416 | A1* | 4/2005 | Morris | 40/649 |
| 2005/0281311 | A1* | 12/2005 | Roberts et al. | 374/106 |
| 2006/0061454 | A1* | 3/2006 | Debord et al. | 340/309.16 |
| 2006/0130734 | A1* | 6/2006 | Koivukunnas et al. | 116/216 |
| 2006/0214788 | A1* | 9/2006 | Ku et al. | 340/539.26 |
| 2007/0067177 | A1* | 3/2007 | Martin et al. | 705/1 |
| 2008/0004372 | A1* | 1/2008 | Prusik et al. | 523/160 |
| 2008/0223929 | A1* | 9/2008 | Togashi et al. | 235/385 |
| 2008/0232426 | A1* | 9/2008 | Welt | 374/102 |
| 2010/0332407 | A1* | 12/2010 | Grieve et al. | 705/332 |

OTHER PUBLICATIONS

Vaikousi et al., "Development of a Microbial Time/Temperature Indicator Prototype for Monitoring the Microbiological Quality of Chilled Foods," Applied and Environmental Microbiology, dated May 2008, vol. 74, No. 10, pp. 3242-3250 (9 pgs.).

Giannakourou et al., "Field Evaluation of the Application of Time Temperature Integrators for Monitoring Fish Quality in the Chill Chain," International Journal of Food Microbiology, dated 2005, vol. 102, pp. 323-336 (14 pgs.).

Tsironi et al., "Predictive Modelling and Selection of Time Temperature Integrators for Monitoring the Shelf Life of Modified Atmosphere Packed Gilthead Seabream Fillets," LWT—Food Science and Technology, dated 2011, vol. 44, pp. 1156-1163 (8 pgs.).

Park et al., "Mathematical Simulation of the Temperature Dependence of Time Temperature Integrator (TTI) and Meat Qualities," KOSFA, Journal of Food Science and Technology, published Jun. 2009, vol. 29, No. 3, pp. 349-355 (7 pgs.).

\* cited by examiner (a) Before displaying TTI indication value (b) After displaying TTI indication value

SYSTEM FOR PROVIDING FOOD EXPIRATION DATE INFORMATION USING TTI AND METHOD FOR PROVIDING FOOD EXPIRATION DATE INFORMATION USING THE SAME

This application is the national phase entry of PCT Application No. PCT/KR2011/003087, filed on Apr. 27, 2011, which claims priority to Korean Application No. 10-2010-0059511, filed on Jun. 23, 2010, the disclosures of which are incorporated herein by reference in their entirety for all purposes.

BACKGROUND

1. Field of the Invention

The present invention relates to a system for providing food shelf-life information using a time-temperature integrator (TTI) and a method for providing food shelf-life information using the same. More particularly, the present invention relates to a system for providing food shelf-life information using a TTI and a method for providing food shelf-life information using the same, which can accurately match an indication value indicated by the TTI and a remaining shelf-life of a food.

2. Background of the Invention

Due to changes in social conditions, and the diversification, advancement, and simplification of food, the interest in safe and convenient food supply systems has increased. People tend to prefer high quality food with the perception of the quality and safety of food beyond the existing quantitative food consumption pattern.

Moreover, as the desire for the quality of the food increases, the need to predict changes in the quality of the food in a scientific manner is required, and in order to improve its competitiveness, it is necessary to minimize the change in the quality of the food during distribution.

To this end, as part of research aimed at predicting the change in the quality of the food with economic costs, the use of time-temperature integrators (TTI) in the distribution of a variety of foods such as seafood, fruits, vegetables, meats, dairy products, etc. has recently been reported.

The time-temperature integrator refers to a kind of sensor that quantitatively indicates the history of accurate time and temperature that the food experiences during storage and transport, and general TTIs are used to predict the quality of the food from a color change due to the time and temperature history.

These TTIs have advantage that the time and temperature history of perishable foods can be easily monitored and the monitoring can be performed at low costs.

In order that the prediction results of the TTI have sufficient confidence, it is required that the TTI be attached to a food in the initial stage when the corresponding food goes through the distribution process and the reaction of the TTI be initiated.

However, in the current food distribution system, the food is exposed to various temperature environments for a predetermined time before the TTI is attached to the food. Accordingly, it was not easy for the food and the TTI to have the same time and temperature history after the TTI is attached to the food and the reaction of the TTI is initiated.

For this reason, even though the TTI is attached to the food, the indication value of the TTI does not match the substantial time and temperature history of the food to which the TTI is attached, and thus the indication value is not reliable, which is problematic.

SUMMARY

Herein disclosed is a system for providing food shelf-life information using a time-temperature integrator (TTI), the system comprising: an input unit which receives TTI information on a TTI itself, food information on a food to which the TTI is to be attached, and distribution history information on the food before the TTI is attached to the food; a calculation unit which calculates a TTI indication value corresponding to a remaining shelf-life of the food based on the TTI information, the food information, and the distribution history information; and an output unit which designates a color corresponding to the remaining shelf-life of the food from colors for each step that can be indicated by the TTI based on time and temperature conditions using the TTI indication value and displays the color.

In an embodiment, the TTI is any one selected from the group consisting of an enzymatic based TTI, a diffusion based TTI, a photosensitive based TTI, a polymer based TTI, and a microbial based TTI. In an embodiment, the TTI information comprises information on any one of time and temperature history of the TTI before the TTI is attached to the food, a type of the TTI, a manufacturer, a catalog number, a serial number, and a production time. In an embodiment, the food is selected from the group consisting of seafood, meat, fruit, vegetable, and dairy product. In an embodiment, the food is selected from the group consisting of a room temperature food, a chilled food, and a frozen food. In an embodiment, the food information comprises information on any one of a type of the food and a distribution method of the food. In an embodiment, the distribution history information comprises temperature and time history of the food before the TTI is attached to the food.

In an embodiment, a barcode or RFID chip containing the TTI information, the food information, and the distribution history information is assigned to the TTI and the food, and the input unit receives the above information through a reader that reads the information contained in the barcode or the RFID chip or receives the above information through wired/wireless communication devices.

In an embodiment, when the TTI is the enzymatic based TTI, the calculation unit calculates the TTI indication value using the following formula:

$$W = k_{0,W} \exp\left(-\frac{E_{a,W}}{RT_{\mathit{eff}}}\right) t_f$$

wherein W is a TTI indication value, $k_{0,W}$ is a reference reaction constant (h−1), $E_{a,W}$ is activation energy (kJ/mol), R is a gas constant (8.314×10$^{-3}$ KJ/mol·K), $T_{\mathit{eff}}$ is a temperature parameter to the shelf-life of the food, and $t_f$ is a time parameter to the shelf-life of the food.

In an embodiment, the temperature parameter $T_{\mathit{eff}}$ is calculated based on a quality value of the food at a time when the TTI is attached to the food, a quality value of the food at a time when the food starts to spoil, and the time parameter of the food.

In an embodiment, the temperature parameter $T_{\mathit{eff}}$ is calculated using the following formula:

$$T_{\text{eff}} = \frac{-E_{a,VBN}}{R\ln\left(\frac{VBN_f - VBN_i}{k_{0,VBN}t_f}\right)}$$

wherein $E_{a,VBN}$ is activation energy (kJ/mol), R is a gas constant (8.314×10$^{-3}$ KJ/mol·K), $VBN_i$ is a quality value of the food at a time when the TTI is attached to the food, $VBN_f$ is a quality value of the food at a time when the food starts to spoil, $K_{0,VBN}$ is a reference reaction constant (h$^{-1}$), and $t_f$ is a time parameter to the shelf-life of the food and is randomly set.

In an embodiment, the quality value $VBN_i$ of the food at the time when the TTI is attached to the food is calculated using the following formula:

$$VBN_i = VBN_0 + \int_0^{t_i} k_{0,VBN}\exp\left(-\frac{E_{a,VBN}}{RT}\right)dt$$

wherein $VBN_0$ is an initial quality value of the food, $t_i$ is a shelf-life of the food before the TTI is attached to the food, $k_{0,VBN}$ is a reference reaction constant (h$^{-1}$), $E_{a,VBM}$ is activation energy (kJ/mol), R is a gas constant (8.314×10$^{-3}$ KJ/mol·K), and T is a temperature history K before the TTI is attached to the food.

In an embodiment, the initial quality value $VBN_0$ of the food is calculated based on the amount of initial volatile basic nitrogen (mg %) of the food measured initially.

In an embodiment, when the TTI is the diffusion based TTI, the calculation unit calculates the TTI indication value using the following formula:

$$W = kt_f = k_{0,W}\exp\left(-\frac{E_{a,W}}{RT_{\text{eff}}}\right)t_f = \frac{1}{m-1}(L_t^{1-m} - L_0^{1-m})$$

wherein W is a TTI indication value, k is a reaction rate constant, $k_{0,W}$ is a reference reaction constant (h$^{-1}$), $E_{a,W}$ is activation energy (kJ/mol), R is a gas constant (8.314×10$^{-3}$ KJ/mol·K), $T_{\text{eff}}$ is a temperature parameter to the shelf-life of the food, $t_f$ is a temperature parameter to the shelf-life of the food, m is a reaction order, $L_0$ is a brightness of the TTI when t is 0, and $L_t$ is a brightness of the TTI when the time is t.

In an embodiment, when the TTI is the photochemical TTI, the calculation unit calculates the TTI indication value using the following formula:

$$W = \frac{I_M}{I_E} = \frac{I_{M\infty}}{I_{E\infty}} + Ae^{-\frac{t_f}{\tau}}$$

$$\tau = \tau_0\exp\left(-\frac{E_{a,\tau}}{RT_{\text{eff}}}\right)$$

wherein W is a TTI indication value, IM is a degree of diffusion of a fluorescent material, $I_{M\infty}$ is an IM when there is no change, IE is a degree of agglomeration of the fluorescent material, $I_{E\infty}$ is an IE when there is no change, A is a constant indicating a color change rate of the fluorescent material, τ is a constant indicating an agglomeration change rate of a chromophore, $\tau_0$ is a reference value of τ, $E_{a,\tau}$ is activation energy (kJ/mol), and R is a gas constant (8.314×10$^{-3}$ KJ/mol·K).

In an embodiment, when the TTI is the polymer based TTI, the calculation unit calculates the TTI indication value using the following formula:

$$W = -k_{0,W}t_f + 1 = 1 - \frac{1}{A\exp(-\beta T_{\text{eff}})}t_f$$

wherein W is a TTI indication value, $k_{0,W}$ is a reference reaction constant (h$^{-1}$), $t_f$ is a time when the food starts to spoil, and A and β are parameters.

In an embodiment, the quality value of the food at the time when the TTI is attached to the food is calculated using the following formula:

$$\ln N_i = \ln N_0 + \int_0^{t_i} k_{0,N}\exp\left(-\frac{E_{a,N}}{RT}\right)dt$$

wherein $\ln N_i$ is a quality value of the food at a time when the TTI is attached to the food, $k_{0,N}$ is a reference reaction constant (h−1), $E_{a,N}$ is activation energy (kJ/mol), R is a gas constant (8.314×10$^{-3}$ KJ/mol·K), T is a temperature before the TTI is attached to the food, and $t_i$ is a shelf-life of the food before the TTI is attached to the food.

In an embodiment, the system further comprises a code assignment unit which assigns the same code information to the TTI, the food, and a color label on which the TTI indication value is displayed. In an embodiment, the input unit, the calculation unit, the output unit, and the code assignment unit are connected through a wired or wireless network.

Also disclosed herein is a method for providing food shelf-life information using a time temperature integrator (TTI), the method comprising the steps of: a) receiving TTI information on a TTI itself, food information on a food to which the TTI is to be attached, and distribution history information on the food before the TTI is attached to the food; b) calculating a TTI indication value corresponding to a remaining shelf-life of the food based on the TTI information, the food information, and the distribution history information; and c) designating a color corresponding to the remaining shelf-life of the food from colors for each step that can be indicated by the TTI based on time and temperature conditions using the TTI indication value and displaying the color.

In an embodiment, step b) comprises the steps of: b1) calculating a quality value of food based on the TTI information, the food information, and the distribution history information; and b2) calculating a TTI indication value corresponding to a remaining shelf-life of the food based on the calculated quality value of the food.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

DETAILED DESCRIPTION

Technical Problem

Figure 1:
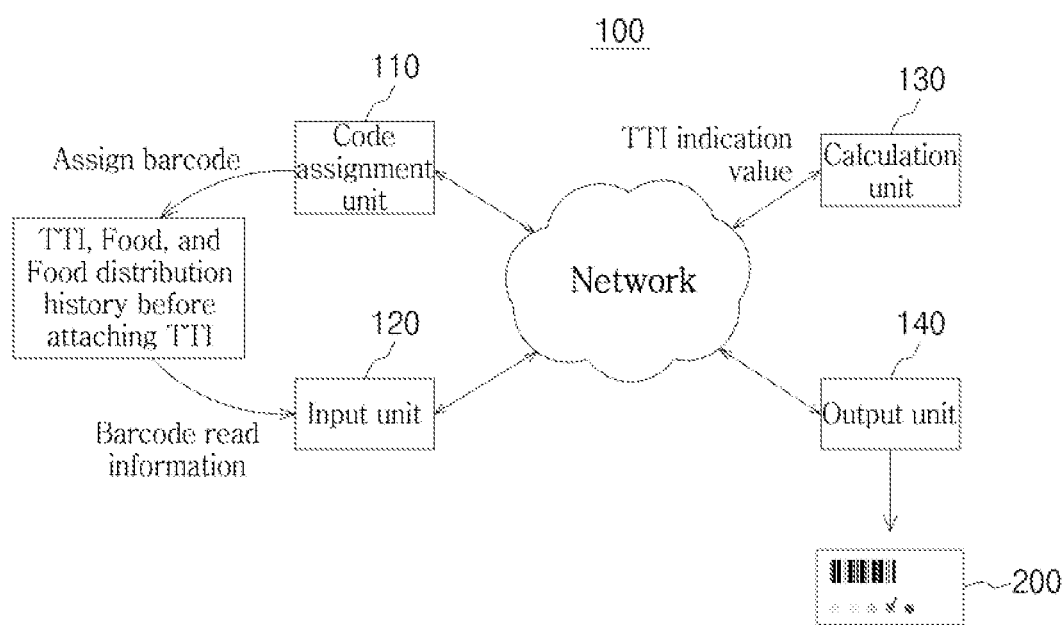
FIG. 1 is a block diagram of a system for providing food shelf-life information in accordance with a preferred embodiment of the present invention.

Accordingly, the present invention has been made to solve the above-described problems, and an object of the present invention is to provide a system for providing food shelf-life information using a time-temperature integrator (TTI) and a method for providing food shelf-life information using the same, which can determine an accurate TTI indication value corresponding to a substantial shelf-life of a food based on the time and temperature history of the corresponding food at a time when the TTI is attached to the food.

Technical Solution

To accomplish the above objects of the present invention, there is provided a system for providing food shelf-life information using a time temperature integrator (TTI), the system comprising: an input unit which receives TTI information on a TTI itself, food information on a food to which the TTI is to be attached, and distribution history information on the food before the TTI is attached to the food; a calculation unit which calculates a TTI indication value corresponding to a remaining shelf-life of the food based on the TTI information, the food information, and the distribution history information; and an output unit which designates a color corresponding to the remaining shelf-life of the food from colors for each step that can be indicated by the TTI based on time and temperature conditions using the TTI indication value and displays the color.

Moreover, the present invention provides a method for providing food shelf-life information using a time temperature integrator (TTI), the method comprising the steps of a) receiving TTI information on a TTI itself, food information on a food to which the TTI is to be attached, and distribution history information on the food before the TTI is attached to the food; b) calculating a TTI indication value corresponding to a remaining shelf-life of the food based on the TTI information, the food information, and the distribution history information; and c) designating a color corresponding to the remaining shelf-life of the food from colors for each step that can be indicated by the TTI based on time and temperature conditions using the TTI indication value and displaying the color.

Advantages

According to the preferred embodiment of the present invention, the TTI indication value corresponding to the shelf-life shown on the food is provided to allow a customer to accurately identify the shelf-life of the corresponding food.

Mode for Invention

Hereinafter, preferred embodiments in accordance with the present invention will be described with reference to the accompanying drawings. It should be noted that in the following description, the same elements will be designated by the same reference numerals even though they are shown in different drawings. Moreover, when it is determined that the detailed description of the related art may unnecessarily obscure the subject matter of the present invention, the description thereof will be omitted. Furthermore, although the preferred embodiments of the present invention will be described below, the technical scope of the present invention is not limited thereto or thereby, but may also be implemented by those skilled in the art.

A time-temperature integrator (TTI) refers to a sensor that quantitatively indicates the time and temperature history that the food experiences during storage and distribution. General TTIs are used to predict the quality of the food indirectly from a color change due to the time and temperature history.

The color change mechanisms of the TTI are based on chemical, physical, and biological reactions of TTI components.

A system for providing food shelf-life information in accordance with a preferred embodiment of the present invention may use any one of an enzymatic based TTI, a diffusion based TTI, a photosensitive based TTI, a polymer based TTI, and a microbial based TTI.

For reference, the enzymatic based TTI is based on a color change caused by a pH decrease due to the enzymatic hydrolysis of a lipid as a substrate. The enzymatic based TTI may be divided into two compartments: one compartment contains a emulsion of lipase, and the other compartment contains a pH indicator and a emulsion of lipid.

Various enzymes and substrates may be used depending on the purpose of use, and the reaction of the TTI is activated by artificial destruction of a barrier that separates the two compartments. The enzymatic hydrolysis of the substrate causes a pH decrease or changes the color of an indicator, or the reaction of the substrate directly changes the color of the indicator.

The diffusion based TTI is based on the diffusion of polymeric materials in a porous substrate, resulting in a color changes with temperature increases.

The polymer based TTI and the photosensitive based TTI use the principle that the formation reaction of a colored polymer or fluorescent material is dependent on the temperature and causes a visible color change.

The microbial based TTI uses the principle that a metabolites produced by microorganisms causes a color change and the production of the metabolites is dependent on the temperature.

FIG. 1 is a block diagram of a system for providing food shelf-life information in accordance with a preferred embodiment of the present invention.

A system 100 for providing food shelf-life information in accordance with a preferred embodiment of the present invention comprises a code assignment unit 110, an input unit 120, a calculation unit 130, and an output unit 140.

The code assignment unit 110 assigns the same code information to a time-temperature integrator (TTI), a food to which the TTI is to be attached, and a color label 200 on which a TTI indication value calculated by the calculation unit 130 is displayed.

Here, the code information includes unique IDs for the TTI, the food, and the color label 200 and may contain TTI information on the TTI itself, food information on the food to which the TTI is to be attached, and distribution history information on the food before the TTI is attached to the food.

The code information assigned by the code assignment unit 110 may be output in the form of a barcode label by a printing device and attached to the TTI, the food, and the color label 200, and a barcode may be printed directly on the color label 200.

Otherwise, a radio frequency identification (RFID) chip containing the code information may be attached to the TTI, the food, and the color label 200.

By assigning the code information, it is possible to fundamentally prevent the TTI and the color label 200 from being artificially manipulated later, thus allowing a customer to identify an accurate shelf-life of the food.

The input unit 120 receives the TTI information, the food information, and the distribution history information.

The input unit 120 may receive the above information through a reader that reads the information contained in the barcode or the RFID chip. Otherwise, the input unit 120 may receive the above information from a manager that manages the TTI and the food through wired/wireless communication devices.

For example, the temperature and time information throughout the distribution history of the food, such as a vehicle transporting the food, a cold storage storing the food, etc., before the TTI is attached to the food may be input remotely to the input device 120 from the vehicle, the storage, etc. through a communication network.

The calculation unit 130 calculates a quality value indicative of the quality of the food based on the TTI information, the food information, and the distribution history information and calculates a TTI indication value corresponding to a remaining shelf-life of the food based on the calculated quality value. The process of calculating the TTI indication value by the calculation unit 130 will be described later.

The output unit 140 serves to designate and display a color corresponding to the remaining shelf-life of the food from colors for each step that can be indicated by the TTI depending on the time and temperature conditions.

Figure 2:
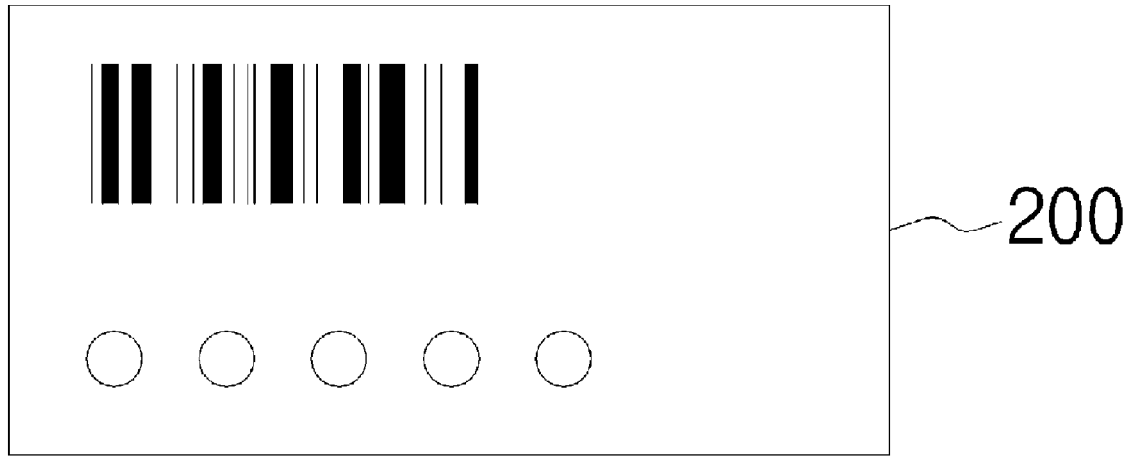
FIG. 2 is a diagram showing that a TTI indication value is displayed on a color label.
Figure 2:
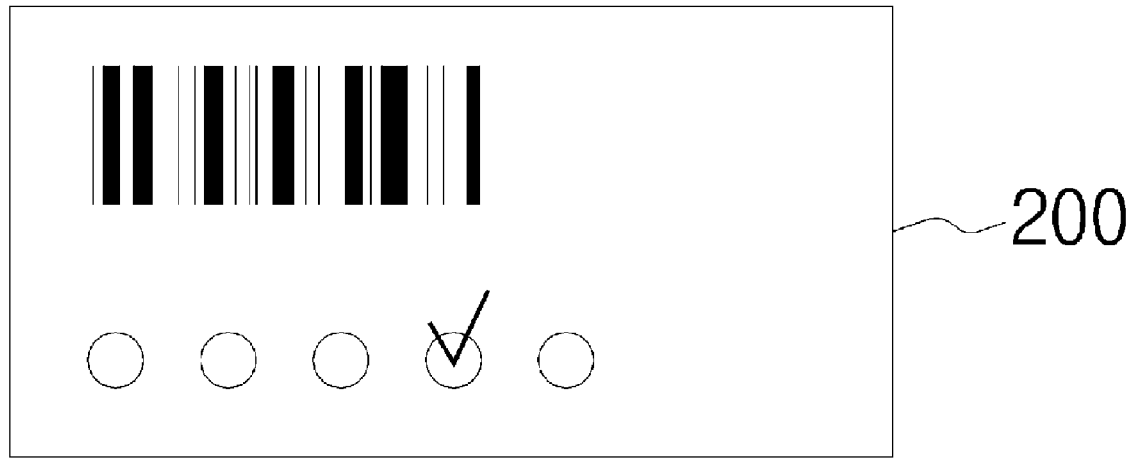
Figure 3:
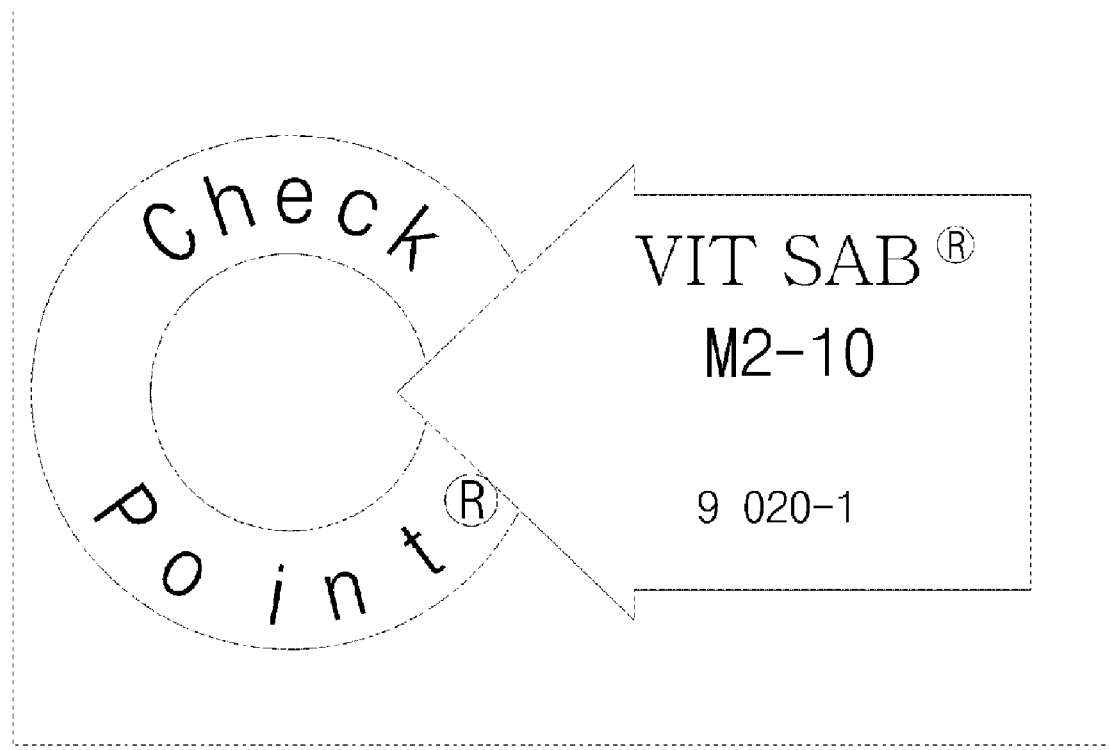
FIGS. 3 to 6 are diagrams showing a color change of a TTI according to the lapse of time.
Figure 4:
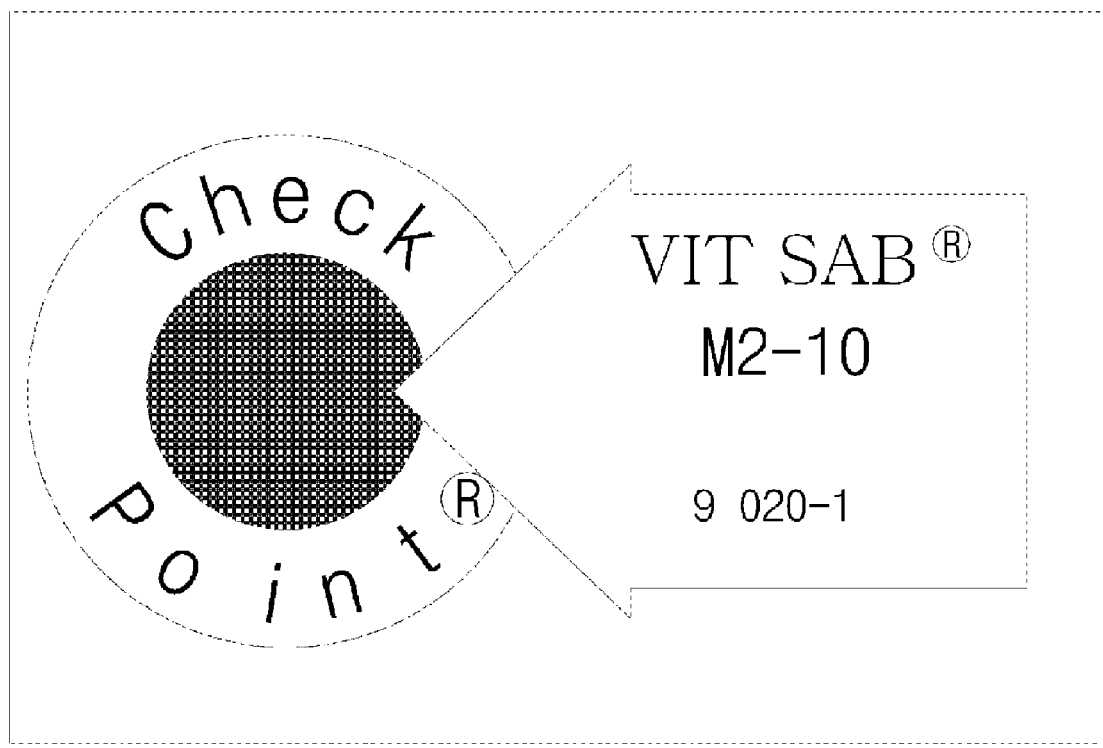
Figure 5:
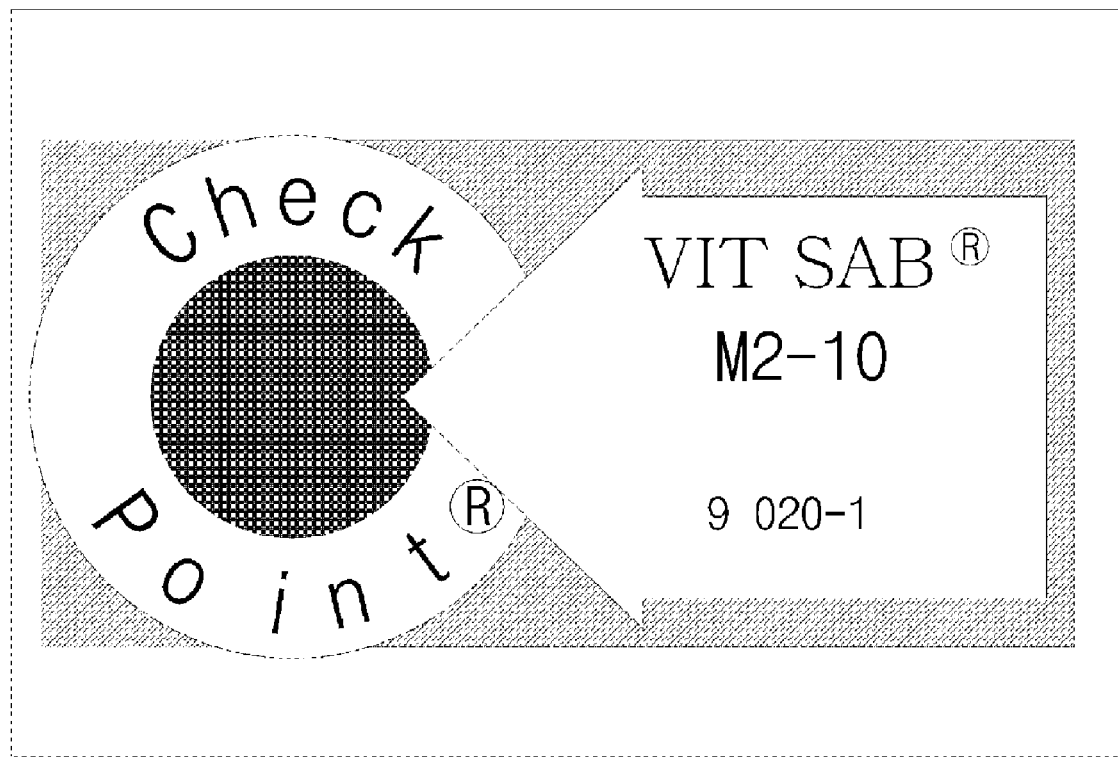
Figure 6:
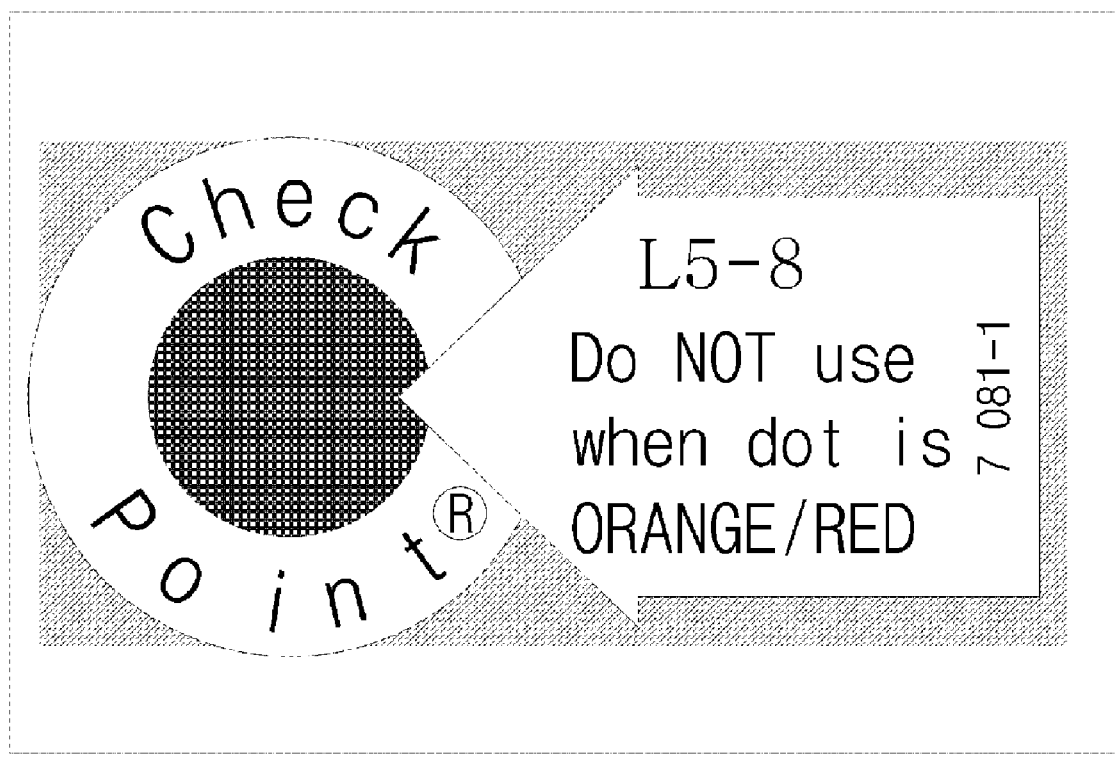

FIG. 2 is a diagram showing that a TTI indication value is displayed on a color label, and FIGS. 3 to 6 are diagrams showing a color change of a TTI according to the lapse of time.

As shown in (a) of FIG. 2, colors for each step that can be indicated by the TTI depending on the time and temperature conditions are displayed in advance and, as shown in (b) of FIG. 2, the output unit 140 checks a TTI color corresponding to the calculated TTI indication value on the color label 200 through a printing means.

Meanwhile, as shown in FIGS. 3 to 6, the color changes depending on the time and temperature conditions and, when the changed color of the TTI changes to the color checked on the color label 200, it can be determined that the shelf-life of the corresponding food expires.

The code assignment unit 110, the input unit 120, the calculation unit 130, and the output unit 140 may be connected through a wired or wireless network to transmit and receive necessary information between each other and, to this end, the respective components 110, 120, 130, and 140 may be provided with wired/wireless communication modules.

Next, the process of calculating the TTI indication value by the calculation unit 130 will be described in detail.

The calculation unit 130 calculates a TTI indication value based on the TTI information, the food information, and the distribution history information as mentioned above.

Here, the TTI information is data including information on any one of time and temperature history of the TTI before the TTI is attached to the food, a type of the TTI, a manufacturer, a catalog number, a serial number, and a production time.

Meanwhile, the food to which the TTI is attached and managed may be seafood, meat, fruit, vegetable, dairy product, etc. and may be a room temperature food, a chilled food, and a frozen food, depending on a distribution method.

The type of the food and the distribution method of the food may be used as the food information of the present invention.

Specifically, the food information is data including information on the type of the food and the distribution method of the food depending on the temperature, and the distribution method of the food depending on the temperature refers to the above-mentioned distribution method of the food, i.e., methods such as room temperature distribution, chilled distribution, and frozen distribution.

The distribution history information is data including information on the temperature and time history of the food before the TTI is attached to the food. Here, the temperature and time history of the food includes all processes throughout the distribution and corresponds to the entire distribution history that the food experiences before the TTI is attached to the food and the reaction is initiated.

The calculation unit 130 calculates the TTI indication value by applying the above information to a formula depending on the type of the TTI.

For example, the calculation unit 130 calculates a TTI indication value of meat using the amount of volatile basic nitrogen (mg %) as a quality value of meat and, when the used TTI is an enzymatic based TTI, the TTI indication value may be calculated using the following formula 1:

$$W = k_{0,W} \exp\left(-\frac{E_{a,W}}{RT_{eff}}\right) t_f \quad \text{[Formula 1]}$$

wherein W is a TTI indication value, $k_{0,W}$ is a reference reaction constant ($h^{-1}$), $E_{a,W}$ is activation energy (kJ/mol), R is a gas constant ($8.314 \times 10^{-3}$ KJ/mol·K), $T_{eff}$ is a temperature parameter to the shelf-life of the food, and $t_f$ is a time parameter to the shelf-life of the food.

In formula 1, the temperature parameter $T_{eff}$ is calculated based on a quality value of the food at a time when the TTI is attached to the food, a quality value of the food at a time when the food starts to spoil, and the time parameter of the food. Specifically, the temperature parameter $T_{eff}$ is calculated using the following formula 2:

$$T_{eff} = \frac{-E_{a,VBN}}{R \ln\left(\frac{VBN_f - VBN_i}{k_{0,VBN} t_f}\right)} \quad \text{[Formula 2]}$$

wherein $E_{a,VBN}$ is activation energy (kJ/mol), R is a gas constant ($8.314 \times 10^{-3}$ KJ/mol·K), $VBN_i$ is a quality value of the food at a time when the TTI is attached to the food, $VBN_f$ is a quality value of the food at a time when the food starts to spoil, $K_{0,VBN}$ is a reference reaction constant ($h^{-1}$), and $t_r$ is a time parameter to the shelf-life of the food and is randomly set.

Here, the quality value $VBN_i$ of the food at the time when the TTI is attached to the food is calculated using the following formula 3, and the quality value $VBN_f$ at the time when the food starts to spoil is set to a specific value based on food hygiene and quality standards.

$$VBN_i = VBN_0 + \int_0^{t_i} k_{0,VBN} \exp\left(-\frac{E_{a,VBN}}{RT}\right) dt \quad \text{[Formula 3]}$$

wherein $VBN_0$ is an initial quality value of the food, $t_f$ is a shelf-life of the food before the TTI is attached to the food, $k_{0,VBN}$ is a reference reaction constant ($h^{-1}$), $E_{a,VBN}$ is activation energy (kJ/mol), R is a gas constant ($8.314 \times 10^{-3}$ KJ/mol·K), and T is a temperature history K before the TTI is attached to the food. Here, the initial quality value $VBN_0$ of the food is calculated based on the amount of initial volatile basic nitrogen (mg %) of the food measured initially.

The quality value of meat may be based on the degree of proliferation of *Pseudomonas* spp. in microorganisms in addition to the method of using volatile basic nitrogen. In this case, the quality value of the food at the time when the TTI is attached to the food may be calculated using the following formula 5, and the quality value of the food at the time when the food starts to spoil may be calculated using the following formula 4:

$$\ln N_i = \ln N_0 + \int_0^{t_i} k_{0,N} \exp\left(-\frac{E_{a,N}}{RT}\right) dt \quad \text{[Formula 4]}$$

wherein $\ln N_i$ is a quality value of the food at a time when the TTI is attached to the food, $k_{0,N}$ is a reference reaction constant ($h^{-1}$), $E_{a,N}$ is activation energy (kJ/mol), R is a gas constant ($8.314 \times 10^{-3}$ KJ/mol·K), T is a temperature before the TTI is attached to the food, and $t_i$ is a shelf-life of the food before the TTI is attached to the food.

Meanwhile, when the diffusion-based TTI is used instead of the enzymatic TTI, the calculation unit 130 may calculate the TTI indication value using the following formula 5:

$$W = kt_f = k_{0,W} \exp\left(-\frac{E_{a,W}}{RT_{eff}}\right) t_f = \frac{1}{m-1}(L_t^{1-m} - L_0^{1-m}) \quad \text{[Formula 5]}$$

wherein W is a TTI indication value, k is a reaction rate constant, $k_{0,W}$ is a reference reaction constant ($h^{-1}$), $E_{a,W}$ is activation energy (kJ/mol), R is a gas constant ($8.314 \times 10^{-3}$ KJ/mol·K), $T_{eff}$ is a temperature parameter to the shelf-life of the food, $t_f$ is a temperature parameter to the shelf-life of the food, m is a reaction order, $L_0$ is a brightness of the TTI when t is 0, and $L_t$ is a brightness of the TTI when the time is t.

When the TTI is the photochemical TTI, the calculation unit 130 may calculate the TTI indication value using the following formula 6:

$$W = \frac{I_M}{I_E} = \frac{I_{M\infty}}{I_{E\infty}} + A e^{-t_f/\tau} \quad \text{[Formula 6]}$$

$$\tau = \tau_0 \exp\left(-\frac{E_{a,\tau}}{RT_{eff}}\right)$$

wherein W is a TTI indication value, $I_M$ is a degree of diffusion of a fluorescent material, $I_{M\infty}$ is an $I_M$ when there is no change, $I_E$ is a degree of agglomeration of the fluorescent material, $I_{E\infty}$ is an $I_E$ when there is no change, A is a constant indicating a color change rate of the fluorescent material, $\tau$ is a constant indicating an agglomeration change rate of a chromophore, $\tau_0$ is a reference value of $\tau$, $E_{a,\tau}$ is activation energy (kJ/mol), and R is a gas constant ($8.314 \times 10^{-3}$ KJ/mol·K).

When the TTI is the polymer-based TTI, the calculation unit 130 may calculate the TTI indication value using the following formula 7 instead of the above formula 6:

$$W = -k_{0,W} t_f + 1 = 1 - \frac{1}{A \exp(-\beta T_{eff})} t_f \quad \text{[Formula 7]}$$

wherein W is a TTI indication value, $k_{0,W}$ is a reference reaction constant ($h^{-1}$), $t_f$ is a time when the food starts to spoil, and A and $\beta$ are parameters.

As such, the calculation unit 130 selects a pre-stored formula based on the type of the TTI and the type of the food and calculates the TTI indication value by applying the received TTI information, food information, and distribution history information to the selected formula.

The TTI indication value calculated in the above manner is output as an indication of a specific color corresponding to an accurate remaining shelf-life of the food and selected from colors for each step that can be indicated by the TTI through the output unit 140 as mentioned above.

As an example of the indication, a method of marking a color corresponding to the remaining shelf-life on the color label 200 on which the colors for each step that can be indicated by the TTI are pre-printed as shown in FIG. 2 may be used.

Otherwise, although not shown, a method of printing a label on which only a specific color corresponding to the shelf-life is shown may be used. For this purpose, the output unit 140 may be provided with a separate printing device that outputs a label that can visualize a specific color corresponding to the remaining shelf-life of the food and display the color.

Figure 7:
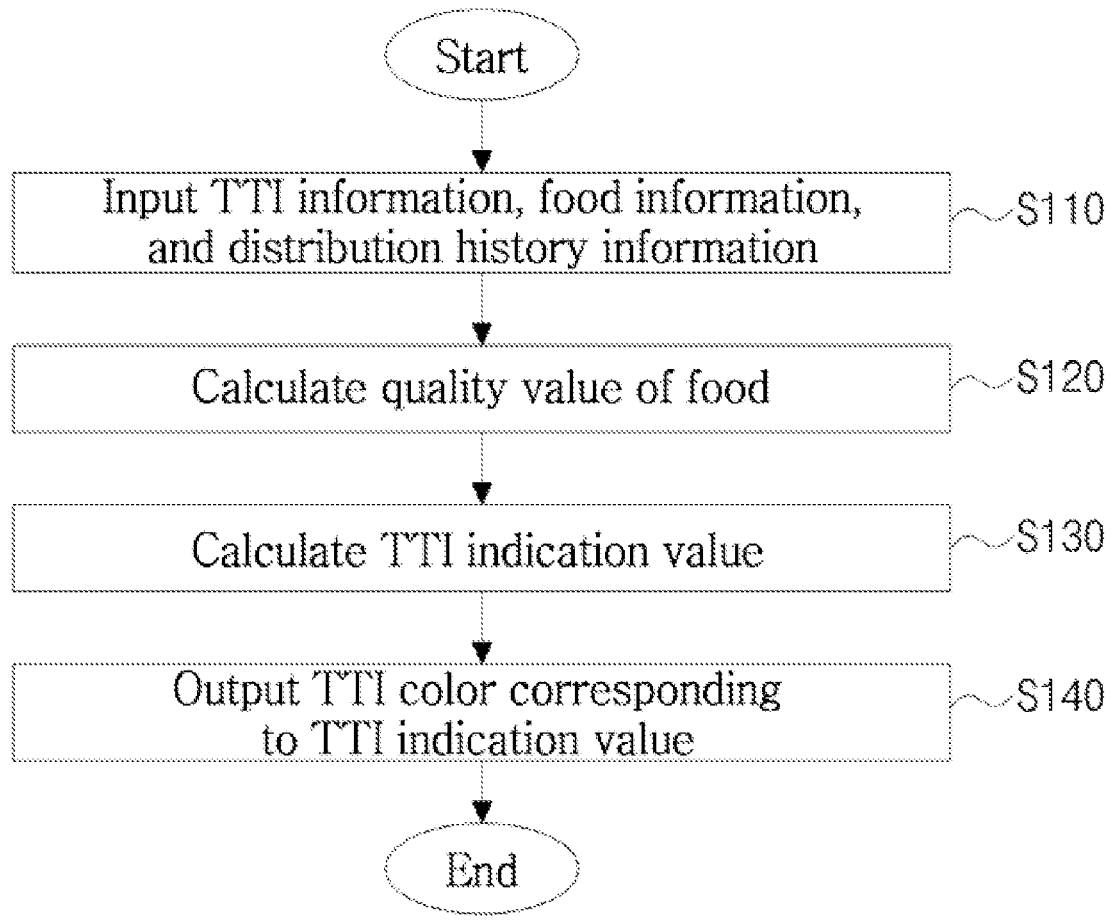
FIG. 7 is a flowchart showing a process for providing food shelf-life information using a system for providing food shelf-life information in accordance with a preferred embodiment of the present invention.

FIG. 7 is a flowchart showing a process for providing food shelf-life information using a system for providing food shelf-life information in accordance with a preferred embodiment of the present invention.

Next, a procedure of providing food shelf-life information using the system 100 for providing food shelf-life information in accordance with a preferred embodiment of the present invention will be described with reference to FIG. 7.

First, the input unit 120 receives TTI information on a TTI itself, food information on a food to which the TTI is to be attached, and distribution history information on the food before the TTI is attached to the food (S110).

Then, the calculation unit 130 calculates a quality value of the food based on the TTI information, the food information, and the distribution history information (S120) and calculates a TTI indication value corresponding to a remaining shelf-life of the food based on the calculated quality value of the food (S130).

When the TTI indication value is calculated, the output unit 140 designates a color corresponding to the remaining shelf-life of the food from colors for each step that can be indicated by the TTI based on time and temperature conditions using the TTI indication value and displays the color (S140).

Here, a barcode or RFID chip containing the TTI information, the food information, and the distribution history information is assigned to the TTI and the food by the code assignment unit 110, and the input unit 120 may receive the above information through a reader that reads the information contained in the barcode or the RFID chip or receive the above information from through wired/wireless communication devices.

The spirit of the present invention has been just exemplified. It will be appreciated by those skilled in the art that various modifications, changes, and substitutions can be made without departing from the essential characteristics of the present invention. Accordingly, the exemplary embodiments disclosed in the present invention and the accompanying drawings are used not to limit but to describe the spirit of the present invention. The scope of the present invention is not limited only to the embodiments and the accompanying drawings. The protection scope of the present invention must be interpreted by the appended claims and it should be interpreted that all spirits within a scope equivalent thereto are included in the appended claims of the present invention.

What is claimed is:

1. A system for providing food shelf-life information using a time-temperature integrator (TTI), the system comprising:
an input unit in which TTI information regarding a TTI itself, food information regarding a food to which the TTI is to be attached, and distribution history information regarding the food before the TTI is attached to the food are input in advance;
a calculation unit which receives the TTI information, the food information, and the distribution history information from the input unit and calculates a TTI indication value corresponding to a remaining shelf-life of the food based on the received information; and
an output unit which receives the TTI indication value from the calculation unit and designates a color corresponding to the remaining shelf-life of the food from colors for each step that can be indicated by the TTI based on time and temperature conditions using the received TTI indication value and displays the color,
wherein the TTI is any one selected from the group consisting of an enzymatic TTI, a diffusion-based TTI, a photochemical TTI, a polymer-based TTI, and a microbial-based TTI,
wherein when the TTI is the diffusion-based TTI, the calculation unit calculates the TTI indication value using the following Formula A:

$$W = kt_f = k_{0,W}\exp\left(-\frac{E_{a,W}}{RT_{eff}}\right)t_f = \frac{1}{m-1}(L_t^{1-m} - L_0^{1-m}); \quad \text{(Formula A)}$$

in Formula A, W is a TTI indication value, k is a reaction rate constant, $k_{0,W}$ is a reference reaction constant ($h^{-1}$), $E_{a,W}$ is activation energy (kJ/mol), R is a gas constant ($8.314\times10^{-3}$ KJ/mol·K), Teff is a temperature parameter to the shelf-life of the food, $t_f$ is a temperature parameter to the shelf-life of the food, m is a reaction order, $L_0$ is a brightness of the TTI when t=0 and $L_t$ is a brightness of the TTI when the time is t,
wherein when the TTI is the photochemical TTI, the calculation unit calculates the TTI indication value using the following Formula B:

$$W = \frac{I_M}{I_E} = \frac{I_{M\infty}}{I_{E\infty}} + Ae^{-\frac{t_f}{\tau}} \quad \text{(Formula B)}$$

$$\tau = \tau_0\exp\left(-\frac{Ea,\tau}{RT_{eff}}\right);$$

In Formula B, W is a TTI indication value, $I_M$ is a degree of diffusion of a fluorescent material, $I_{M\infty}$ is an $I_M$ when there is no change, $I_E$ is a degree of agglomeration of the fluorescent material, $I_{E\infty}$ is an $I_E$ when there is no change, A is a constant indicating a color change rate of the fluorescent material, τ is a constant indicating an agglomeration change rate of a chromophore, $\tau_0$ is a reference value of τ, $E_{a,\tau}$ is activation energy (kJ/mol), and R is a gas constant ($8.314\times10^{-3}$ KJ/mol·K), wherein when the TTI is the polymer-based TTI, the calculation unit calculates the TTI indication value using the following Formula C:

$$W = -k_{0,W}t_f + 1 = 1 - \frac{1}{A\exp(-\beta T_{eff})}t_f; \quad \text{(Formula C)}$$

in Formula C, W is a TTI indication value, $k_{0,W}$ is a reference reaction constant ($h^{-1}$), $t_f$ is a time when the food starts to spoil, and A and β are parameters.

2. The system of claim 1, wherein the TTI information comprises information on any one of time and temperature history of the TTI before the TTI is attached to the food, a type of the TTI, a manufacturer, a catalog number, a serial number, and a production time.

3. The system of claim 1, wherein the food is selected from the group consisting of seafood, meat, fruit, vegetable, and dairy product.

4. The system of claim 1, wherein the food is selected from the group consisting of a room temperature food, a chilled food, and a frozen food.

5. The system of claim 1, wherein the food information comprises information on any one of a type of the food and a distribution method of the food.

6. The system of claim 1, wherein the distribution history information comprises temperature and time history of the food before the TTI is attached to the food.

7. The system of claim 1, wherein a barcode or RFID chip containing the TTI information, the food information, and the distribution history information is assigned to the TTI and the food, and
wherein the input unit receives the above information through a reader that reads the information contained in the barcode or the RFID chip or receives the above information through wired/wireless communication devices.

8. The system of claim 1, wherein when the TTI is the enzymatic based TTI, the calculation unit calculates the TTI indication value using the following formula:

$$W = k_{0,W}\exp\left(-\frac{E_{a,W}}{RT_{eff}}\right)t_f$$

wherein W is a TTI indication value, $k_{0,W}$ is a reference reaction constant ($h^{-1}$), $E_{a,W}$ is activation energy (kJ/mol), R is a gas constant ($8.314\times10^{-3}$ KJ/mol·K), $T_{eff}$ is a temperature parameter to the shelf-life of the food, and $t_f$ is a time parameter to the shelf-life of the food.

9. The system of claim 8, wherein the temperature parameter $T_{eff}$ is calculated based on a quality value of the food at a time when the TTI is attached to the food, a quality value of the food at a time when the food starts to spoil, and the time parameter of the food.

10. The system of claim 9, wherein the temperature parameter $T_{eff}$ is calculated using the following formula:

$$T_{eff} = \frac{-E_{a,VBN}}{R\ln\left(\frac{VBN_f - VBN_i}{k_{0,VBN} t_f}\right)}$$

wherein $E_{a,VBN}$ is activation energy (kJ/mol), R is a gas constant ($8.314\times10^{-3}$ KJ/mol·K), $VBN_i$ is a quality value of the food at a time when the TTI is attached to the food, $VBN_f$ is a quality value of the food at a time when the food starts to spoil, $K_{0,VBN}$ is a reference reaction constant ($h^{-1}$), and $t_f$ is a time parameter to the shelf-life of the food and is randomly set.

11. The system of claim 10, wherein the quality value $VBN_i$ of the food at the time when the TTI is attached to the food is calculated using the following formula:

$$VBN_i = VBN_0 + \int_0^{\tau_i} k_{0,VBN} \exp\left(-\frac{E_{a,VBN}}{RT}\right) dt$$

wherein $VBN_0$ is an initial quality value of the food, $t_i$ is a shelf-life of the food before the TTI is attached to the food, $k_{0,VBN}$ is a reference reaction constant ($h^{-1}$), $E_{a,VBM}$ is activation energy (kJ/mol), R is a gas constant ($8.314\times10^{-3}$ KJ/mol·K), and T is a temperature history K before the TTI is attached to the food.

12. The system of claim 11, wherein the initial quality value $VBN_0$ of the food is calculated based on the amount of initial volatile basic nitrogen (mg %) of the food measured initially.

13. The system of claim 9, wherein the quality value of the food at the time when the TTI is attached to the food is calculated using the following formula:

$$\ln N_i = \ln N_0 + \int_0^{\tau_i} k_{0,N} \exp\left(-\frac{E_{a,N}}{RT}\right) dt$$

wherein $\ln N_i$ is a quality value of the food at a time when the TTI is attached to the food, $k_{0,N}$ is a reference reaction constant ($h^{-1}$), $E_{a,N}$ is activation energy (kJ/mol), R is a gas constant ($8.314\times10^{-3}$ KJ/mol·K), T is a temperature before the TTI is attached to the food, and $t_i$ is a shelf-life of the food before the TTI is attached to the food.

14. The system of claim 1, further comprising a code assignment unit which assigns the same code information to the TTI, the food, and a color label on which the TTI indication value is displayed.

15. The system of claim 14, wherein the input unit, the calculation unit, the output unit, and the code assignment unit are connected through a wired or wireless network.

\* \* \* \* \*